(12) United States Patent
Liu et al.

(10) Patent No.: US 11,807,672 B2
(45) Date of Patent: *Nov. 7, 2023

(54) CONJUGATES OF ISLET NEOGENESIS PEPTIDES AND ANALOGS, AND METHODS THEREOF

(71) Applicant: SHENZHEN HIGHTIDE BIOPHARMACEUTICAL, LTD., Shenzhen (CN)

(72) Inventors: Liping Liu, Manassas, VA (US); Ru Bai, Shenzhen (CN)

(73) Assignee: Shenzhen HighTide Biopharmaceutical, Ltd., Shenzhen (CN)

( * ) Notice: Subject to any disclaimer, the term of this patent is extended or adjusted under 35 U.S.C. 154(b) by 397 days.

This patent is subject to a terminal disclaimer.

(21) Appl. No.: 17/062,622

(22) Filed: Oct. 4, 2020

(65) Prior Publication Data

US 2021/0122797 A1 Apr. 29, 2021

Related U.S. Application Data

(63) Continuation of application No. 16/074,073, filed as application No. PCT/CN2017/076190 on Mar. 9, 2017, now Pat. No. 10,829,527.

(60) Provisional application No. 62/306,119, filed on Mar. 10, 2016.

(51) Int. Cl.
| | |
|---|---|
| *C07K 14/47* | (2006.01) |
| *A61K 38/26* | (2006.01) |
| *A61K 35/39* | (2015.01) |
| *A61K 38/00* | (2006.01) |
| *C12N 5/071* | (2010.01) |

(52) U.S. Cl.
CPC .......... *C07K 14/4705* (2013.01); *A61K 35/39* (2013.01); *A61K 38/26* (2013.01); *C07K 14/4723* (2013.01); *C07K 14/4726* (2013.01); *C12N 5/0676* (2013.01); *A61K 38/00* (2013.01); *C07K 2319/30* (2013.01); *C12N 2501/335* (2013.01); *C12N 2501/998* (2013.01)

(58) Field of Classification Search
None
See application file for complete search history.

(56) References Cited

U.S. PATENT DOCUMENTS 10,829,527 B2 * 11/2020 Liu ..................... C12N 5/0676

OTHER PUBLICATIONS

Tonne et al. "70. Pancreatic Gene Delivery for Diabetes Therapy" Molecular Therapy 20(S1):S29 (Year: 2012).*
Chen et al. "Fusion Protein Linkers: Property, Design and Functionality" Adv Drug Deliv Rev. 65:1357-1369. (Year: 2013).*

* cited by examiner

*Primary Examiner* — Sudhakar Katakam
*Assistant Examiner* — Zachary J Miknis
(74) *Attorney, Agent, or Firm* — Milstein Zhang & Wu LLC

(57) ABSTRACT

The invention provides novel compounds, in particular peptide and peptide analogs, which exhibit functionalities useful for treating a variety of diseases and conditions, particularly diseases and conditions relating to diabetes. The compounds of the invention are also useful for treating impaired pancreatic function, treating metabolic diseases, ex vivo islet induction, expansion and proliferation for transplantation, increasing the survival of transplanted islets in vivo, promoting neuroprotection or nerve regeneration, promoting liver regeneration, and inhibiting inflammation.

9 Claims, 3 Drawing Sheets

Specification includes a Sequence Listing.

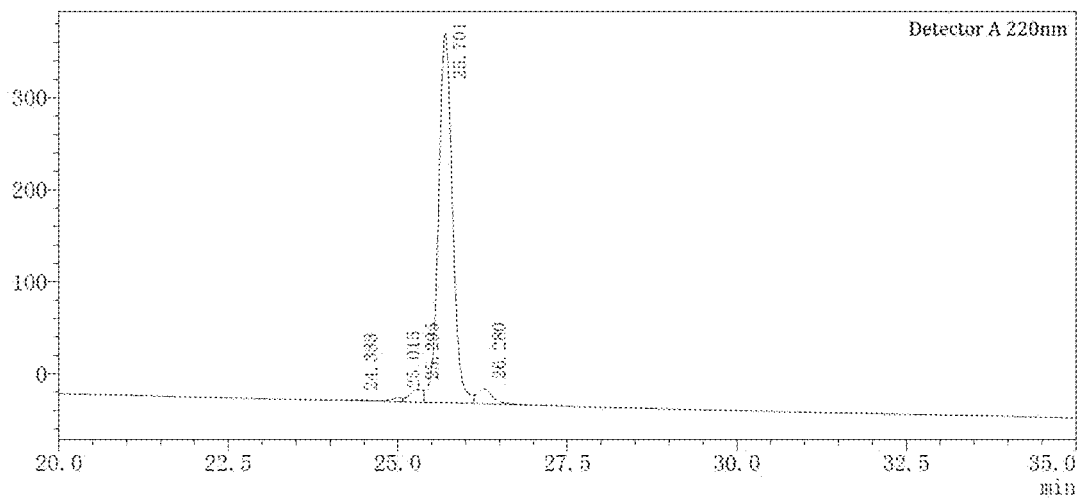
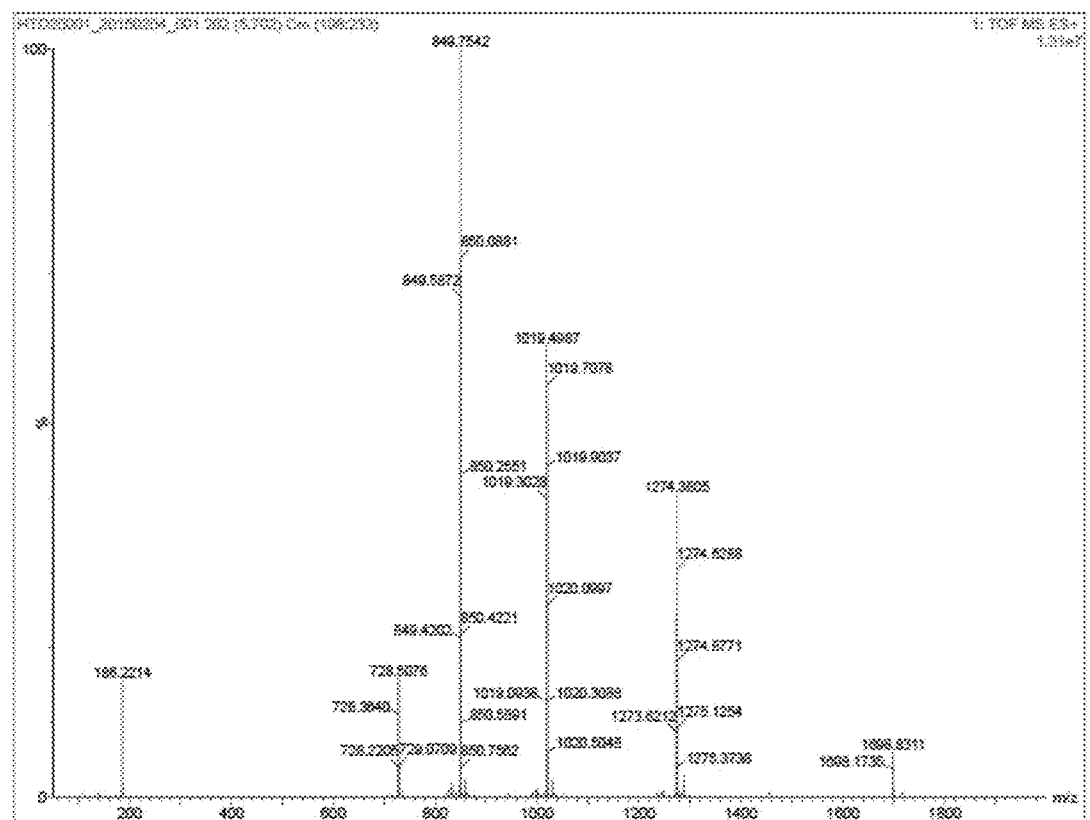
FIG. 1. HPLC chromatogram and MS spectrum of peptide 1
(a): HPLC chromatogram; (b): MS spectrum

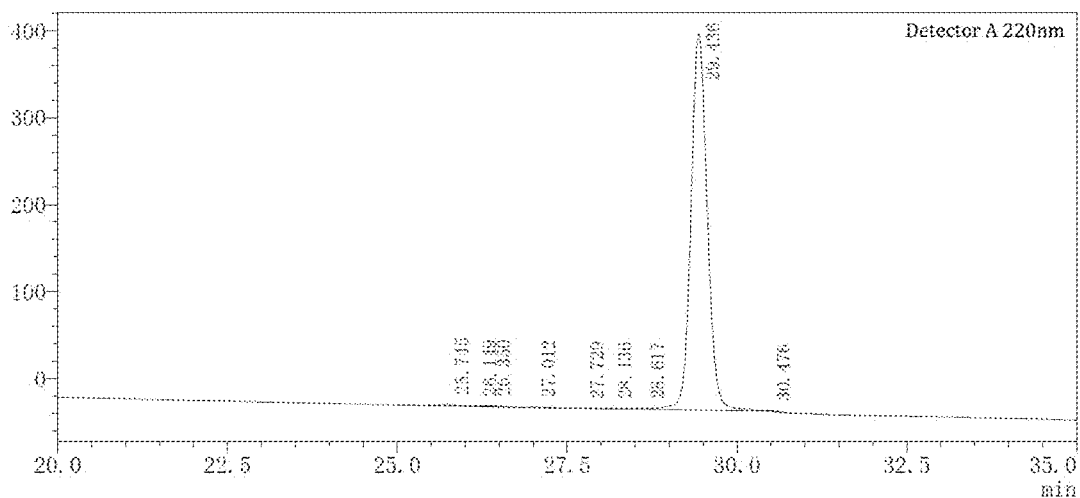
(a)
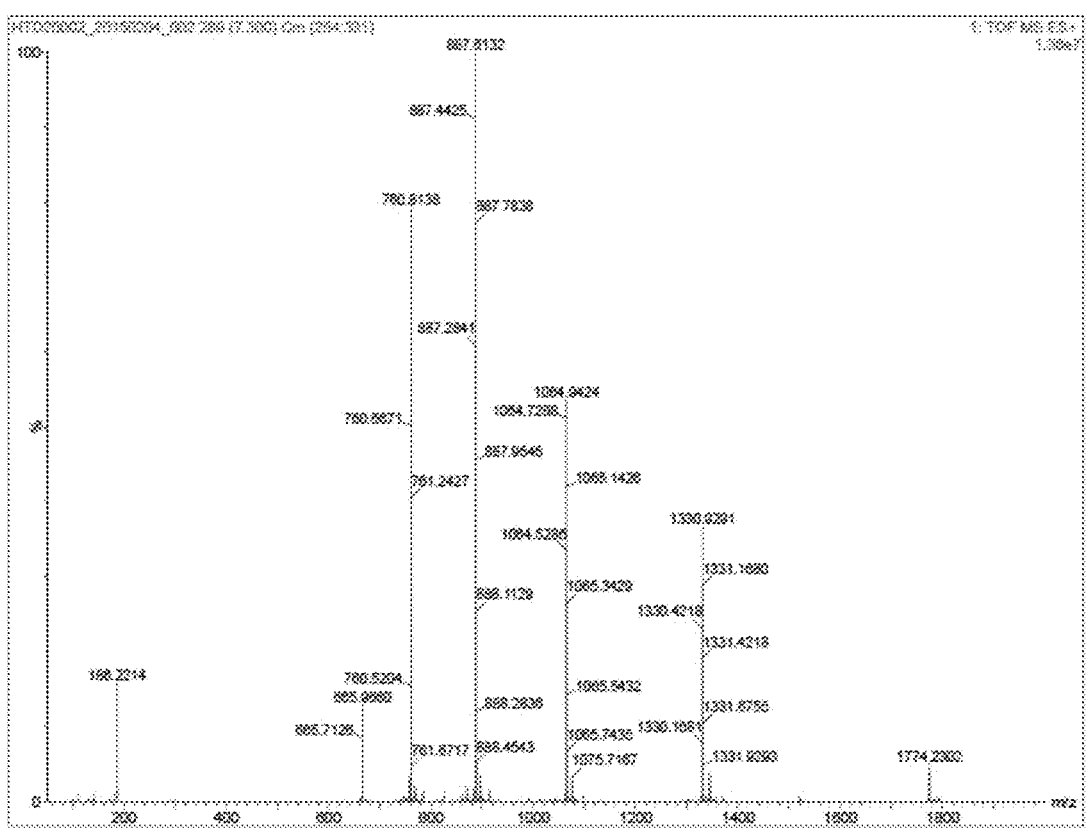
(b)
FIG. 2. HPLC chromatogram and MS spectrum of peptide 2
(a): HPLC chromatogram; (b): MS spectrum

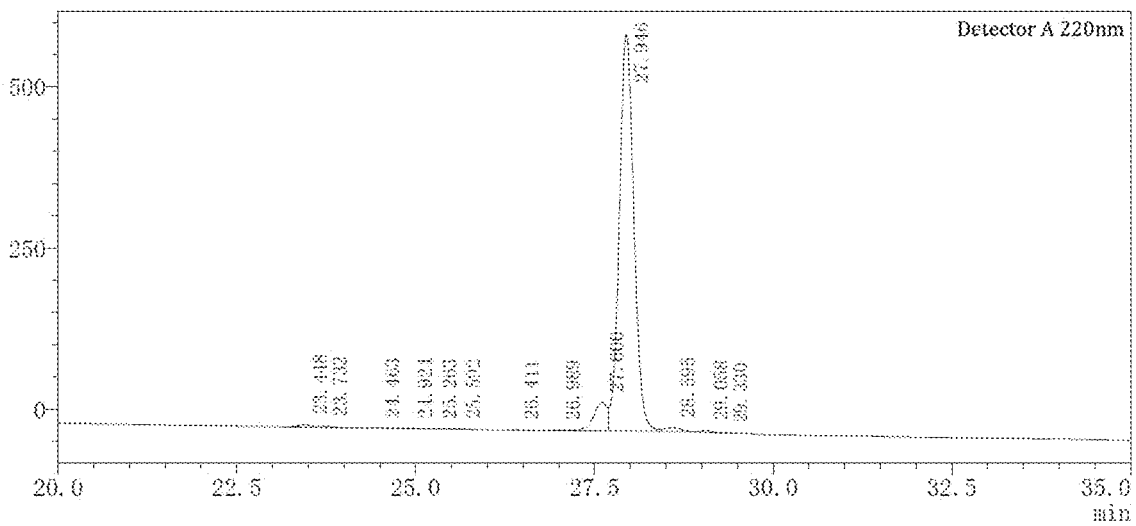
(a)
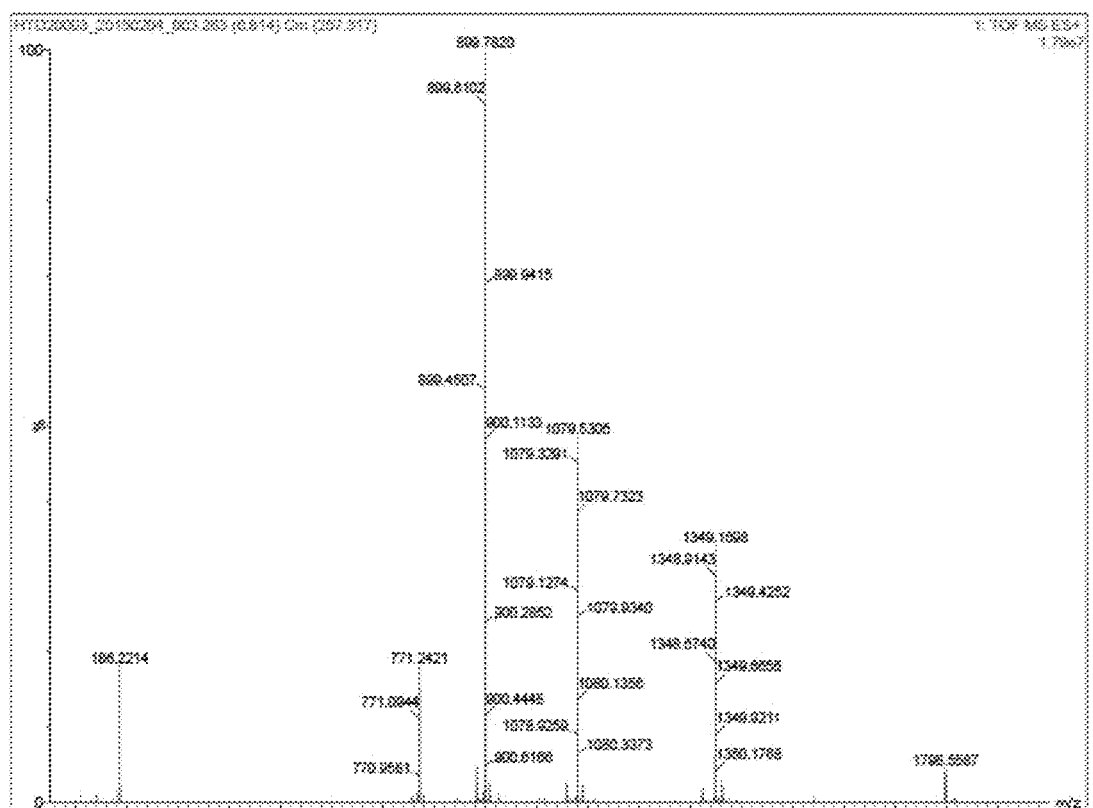
(b)
FIG. 3. HPLC chromatogram and MS spectrum of peptide 3
(a): HPLC chromatogram; (b): MS spectrum

CONJUGATES OF ISLET NEOGENESIS PEPTIDES AND ANALOGS, AND METHODS THEREOF

PRIORITY CLAIMS AND RELATED APPLICATIONS

This application is a continuation of and claims the benefit of priority to U.S. Ser. No. 17/062,622, which is the U.S. national phase of and claims priority to PCT/CN2017/076190, filed Mar. 9, 2017, which claims the benefit of priority from U.S. Provisional Application No. 62/306,119, filed Mar. 10, 2016, the entire content of each of which is incorporated herein by reference.

SEQUENCE LISTING

The instant application contains a Sequence Listing which has been filed electronically in ASCII format and is hereby incorporated by reference in its entirety. Said ASCII copy, created on Jan. 4, 2019, is named SHB006CON_SL.txt and is 40,764 bytes in size.

TECHNICAL FIELD OF THE INVENTION

The invention generally relates to the field of medicine and pharmaceuticals, and more specifically to peptide therapies for treating diabetes and other diseases.

BACKGROUND OF THE INVENTION

Diabetes mellitus (DM) is a chronic disease requiring continuous medical care. In a simple term, DM results when pancreatic beta cells are unable to maintain adequate insulin secretion to maintain glucose homeostasis. There are two main types of DM: type 1 DM (T1D) and type 2 DM (T2D). T1D results from the body's failure to produce insulin, and requires the patient to administer insulin daily. T2D results from insulin resistance, a condition in which cells fail to use insulin properly. There are many approved non-insulin therapies for T2D. However, there is a large portion of late stage T2D patients requiring insulin administration due to the loss of β-cell function as the disease progresses.

Development of diabetes is associated with substantial losses in pancreatic beta cell mass. At the time of diagnosis, over 90% of beta cell mass has been lost in T1D patients, and approximately 50% has been lost in T2D patients. Many attempts have been made in quest for a potential stimulus for β-cell regeneration, which is considered as the optimal disease modifying treatment for both T1D and T2D.

In the past decades, investigators have shown that islet neogenesis-associated protein (INGAP) from hamster, human proIslet peptide (HIP), glucagon like peptide-1 (GLP-1), islet endocrine neuropeptide vasoactive intestinal peptide (VIP), epidermal growth factor and gastrin, and others, are capable of inducing pancreatic progenitor cells, located in the nonendocrine fraction of the pancreas, to differentiate into fully functional islets in various animal models. Among these compounds, INGAP peptide (INGAP-PP), a 15-mer peptide derived from the sequence of INGAP at amino acids 104-118, has been shown to induce islet neogenesis in multiple animal models, reverse streptozotocin (STZ) induced diabetes in mice, increase C-peptide secretion in T1D patients, and improve glycemic control in T2D patients. Additional biological effects of INGAP-PP have been reported, including dose dependent stimulation of expansion of β-cell mass, β-cell replication, reduced β-cell apoptosis, and increased insulin secretion. In human studies, there was an effect with an improvement of glucose homeostasis, confirmed by HbA1c reduction at 90 days in patients with T2D, and by a significant increase in C-peptide secretion in patients with T1D. However, the short plasma half-life of INGAP-PP and the need for administration in a high dose have significantly limited clinical applications of this peptide.

HIP, the bioactive peptide encoded by a portion of the human regenerating islet-derived 3 alpha (REG3A) gene, is the human homolog of the INGAP peptide. Previous studies have shown that treatment of human pancreatic ductal tissues with HIP stimulated the production of insulin. Administration of HIP improved glycemic control and increased islet number in diabetic mice. The stabilized form of HIP has been tested in a single ascending dose clinical trial with the goal of exploring the tolerability, safety and pharmacokinetics. It is of note that daily doses of 60, 120, 240, 480, and 720 mg were used in the trial. Like the INGAP-PP, the high dose is expected to significantly limit clinical applications of this peptide.

Thus, there exists a need to develop additional drugs for treatment of diabetes or other diseases associated with impaired pancreatic function.

SUMMARY OF THE INVENTION

The invention is based in part on the discovery of novel fusion peptides combining INGAP-PP or HIP peptides and analogs with GLP-1 receptor agonists, epidermal growth factor receptor agonists, or Cathelicidin antimicrobial peptides or analogs. The peptides and analogs disclosed herein can be used for treating various diseases and conditions associated with impaired pancreatic function, treating metabolic diseases (e.g., diabetes, both type 1 and type 2 diabetes, prediabetes, metabolic syndrome, islets induction, expansion and proliferation for transplantation), promoting neuroprotection or nerve regeneration, promoting liver regeneration, and inhibiting inflammation.

In one aspect, the invention generally relates to a compound having the formula of (I):

wherein X is selected from INGAP-PP or an analog thereof, or HIP or an analog thereof; L is a linker covalently bonded to X; and Y is a GLP-1 receptor agonist.

In another aspect, the invention generally relates to a compound having the formula of (II):

wherein X is selected from INGAP-PP or an analog thereof, or HIP or an analog thereof; L is a linker covalently bonded to X; and Y is an epidermal growth factor receptor agonist.

In yet another aspect, the invention generally relates to a compound having the formula of (III):

wherein X is selected from INGAP-PP or an analog thereof, or HIP or an analog thereof; L is a linker covalently bonded to X; and Y is a cathelicidin antimicrobial peptide or an analog thereof.

In yet another aspect, the invention generally relates to a compound having the formula of (IV):

wherein X is selected from INGAP-PP or an analog thereof, or HIP or an analog thereof; L is a linker covalently bonded to X; and Y is a GLP-1 receptor agonist.

In yet another aspect, the invention generally relates to a compound having the formula of (V):

Y-L-X            (V)

wherein X is selected from INGAP-PP or an analog thereof, or HIP or an analog thereof; L is a linker covalently bonded to X; and Y is an epidermal growth factor receptor agonist.

In yet another aspect, the invention generally relates to a compound having the formula of (VI):

Y-L-X            (VI)

wherein X is selected from INGAP-PP or an analog thereof, or HIP or an analog thereof; L is a linker covalently bonded to X; and Y is a cathelicidin antimicrobial peptide or an analog thereof.

In yet another aspect, the invention generally relates to a compound comprising the sequence of:

(SEQ ID NO: 111)
HGEGT FTSDL SKQME EEAVR LFIEW LKNGG GGSIG LHDPS

HGTLP NGS-NH2

In yet another aspect, the invention generally relates to a compound comprising the sequence of:

(SEQ ID NO: 112)
HGEGT FTSDL SKQME EEAVR LFIEW LKNAE AAAKI GLHDP

SHGTL PNGS-NH2

In yet another aspect, the invention generally relates to a compound comprising the sequence of:

(SEQ ID NO: 113)
HGEGT FTSDL SKQME EEAVR LFIEW LKNGG GGSIW IGLHD

PSHGT LPNGS-NH2

In yet another aspect, the invention generally relates to a compound comprising the sequence of:

(SEQ ID NO: 114)
IGLHD PSHGT LPAGS GGGGS HGEGT FTSDL SKQME EEAVR

LFIEW LKN

In yet another aspect, the invention generally relates to a compound comprising the sequence of:

(SEQ ID NO: 115)
IGLHD PSHGT LPAGS GGGGG GHGEG TFTSD LSKQM EEEAV

RLFIE WLKN

In yet another aspect, the invention generally relates to a compound comprising the sequence of:

(SEQ ID NO: 116)
IGLHD PSHGT LPAGS AEAAA KHGEG TFTSD LSKQM EEEAV

RLFIE WLKN

In yet another aspect, the invention generally relates to a compound comprising the sequence of:

(SEQ ID NO: 117)
LLGDF FRKSK EKIGK EFKRI VQRIK DFLRN LVPRT ESGGG

GSIGL HDPSH GTLPN GS-NH2

In yet another aspect, the invention generally relates to a compound comprising the sequence of:

(SEQ ID NO: 118)
LLGDF FRKSK EKIGK EFKRI VQRIK DFLRN LVPRT ESAEA

AAKIG LHDPS HGTLP NGS-NH2

In yet another aspect, the invention generally relates to a compound comprising the sequence of:

(SEQ ID NO: 119)
IGLHD PSHGT LPAGS GGGGS LLGDF FRKSK EKIGK EFKRI

VQRIK DFLRN LVPRT ES

In yet another aspect, the invention generally relates to a compound comprising the sequence of:

(SEQ ID NO: 120)
IGLHD PSHGT LPAGS AEAAA KLLGD FFRKS KEKIG KEFKR

IVQRI KDFLR NLVPR TES.

In yet another aspect, the invention generally relates to a composition comprising a compound disclosed herein.

In yet another aspect, the invention generally relates to a method for ameliorating a sign or symptom associated with impaired pancreatic function. The method includes administering a compound disclosed herein.

In yet another aspect, the invention generally relates to a method for stimulating pancreatic islet cell growth. The method includes contacting a pancreatic islet cell with a compound disclosed herein, whereby proliferation of the pancreatic islet cell is stimulated.

In yet another aspect, the invention generally relates to a method of producing a population of pancreatic islet cells. The method includes contacting one or more pancreatic islet cells in vitro with a compound disclosed herein, whereby proliferation of the one or more pancreatic islet cells are stimulated and a population of pancreatic islet cells is produced.

In yet another aspect, the invention generally relates to a method for increasing the number of pancreatic islet cells in a subject. The method includes administering a compound disclosed herein.

In yet another aspect, the invention generally relates to a method for ameliorating a sign or symptom associated with a metabolic disease in a subject. The method includes administering a compound disclosed herein.

In yet another aspect, the invention generally relates to a method of reducing in a diabetic subject impaired glucose tolerance, blood glucose, fasting blood glucose, postprandial blood glucose, insulin deficiency, fasting hyperinsulinemia, insulin resistance, impaired fasting insulin levels, glycosylated hemoglobin (HbA1c), arginine-stimulated C-peptide (AUC), or a combination thereof. The method includes administering a compound disclosed herein.

In yet another aspect, the invention generally relates to a method for promoting neuroprotection or nerve regeneration, comprising contacting a nerve cell with a compound disclosed herein.

In yet another aspect, the invention generally relates to a method for promoting liver regeneration, comprising contacting a liver cell with a compound disclosed herein.

In yet another aspect, the invention generally relates to a method for inhibiting inflammation, comprising administering a compound disclosed herein.

BRIEF DESCRIPTION OF THE DRAWINGS

FIG. 1 shows the HPLC chromatogram and MS spectrum of Peptide 1.

FIG. 2 shows the HPLC chromatogram and MS spectrum of Peptide 2.

FIG. 3 shows the HPLC chromatogram and MS spectrum of Peptide 3.

DETAILED DESCRIPTION OF THE INVENTION

The present invention provides compounds, in particular peptide and peptide analogs, which exhibit functionalities useful for treating a variety of diseases and conditions, particularly diseases and conditions relating to diabetes. The peptides and analogs of the invention are additionally useful for treating impaired pancreatic function, treating metabolic diseases, ex vivo islet induction, expansion and proliferation for transplantation, increasing the survival of transplanted islets in vivo, promoting neuroprotection or nerve regeneration, promoting liver regeneration, and inhibiting inflammation.

Previously designed peptide analogs of INGAP-PP or HIP showed marked improved pharmaceutical properties. Exemplary INGAP-PP and HIP peptides analogs are provided in Table 1 and Table 2. (See, PCT/CN2014/073483 and PCT/CN2013/072771, each of which is incorporated herein by reference in its entirety for all purposes.)

The present invention discloses the design and synthesis of fusion peptides combining INGAP-PP or HIP peptides and analogs with GLP-1 receptor agonists, epidermal growth factor receptor agonists, or Cathelicidin antimicrobial peptides (CAMP) or analogs. These conjugated molecules are envisioned to provide synergistic efficacy in β-cell mass and functions restoration, glucose homeostasis, thereby providing related advantages as well.

TABLE 1

Exemplary INGAP-PP Analogs

| Peptide Name/ SEQ ID NO | Sequence |
| --- | --- |
| INGAP-PP (1) | H-IGLHDPSHGTLPNGS-OH |
| INGAP-PP (6) | H-IGLHAPSHGTLPNGS-OH |
| INGAP-PP (7) | H-IGLHDPSHGTLPAGS-OH |
| INGAP-PP (8) | H-IGLHAPSHGTLPAGS-OH |
| INGAP-PP (9) | H-IGLHDPSHGTLPAGSK-OH |
| INGAP-PP (10) | H-IGLHDPSHGTLP(Aib)GS-OH |
| INGAP-PP (11) | H-IGLHDPSHGTLP(N-methyl-L-Alanine)GS-OH |
| INGAP-PP (12) | Ac-IGLHDPSHGTLPAGS-OH |
| INGAP-PP (13) | H-(D-Isoleucine)GLHDPSHGTLPAGS-OH |

TABLE 1-continued

Exemplary INGAP-PP Analogs

| Peptide Name/ SEQ ID NO | Sequence |
| --- | --- |
| INGAP-PP (14) | H-(L-NorValine)GLHDPSHGTLPAGS-OH |
| INGAP-PP (15) | H-(L-NorLeucine)GLHDPSHGTLPAGS-OH |
| INGAP-PP (16) | Ac-IGLHDPSHGTLPNGS-OH |
| INGAP-PP (17) | H-(D-Isoleucine)GLHDPSHGTLPNGS-OH |
| INGAP-PP (18) | H-IGLHDPSHGTEPNGS-OH |
| INGAP-PP (19) | H-IGLHDPSQGTLPNGS-OH |
| INGAP-PP (20) | H-IGLHDPTHGTLPNGS-OH |
| INGAP-PP (21) | H-IGLHDPSHGTLPNGE-OH |
| INGAP-PP (22) | H-IGLHDPSHGTLPNGK-OH |
| INGAP-PP (23) | H-IGLHDPSHGTLPAGK-OH |
| INGAP-PP (24) | H-IGLHDPSHGTEPAGS-OH |
| INGAP-PP (25) | H-IGLHDPSQGTLPAGS-OH |
| INGAP-PP (26) | H-IGLHDPTHGTLPAGS-OH |
| INGAP-PP (27) | H-IGLHDPSHGTLPAGE-OH |
| INGAP-PP (28) | H-IGLHDPSHGTLPAG-NH2 |
| INGAP-PP (29) | Ac-IGLHDPSHGTLPAGS-NH2 |
| INGAP-PP (30) | Ac-IGLHDPSHGTLPAG-NH2 |
| INGAP-PP (31) | Ac-IGLHDPSHGTLPNGS-NH2 |
| INGAP-PP (32) | H-IGLHDPSHGTLPNGS-NH2 |
| INGAP-PP (33) | H-IGLHDPSHGTLPNGSC-OH |
| INGAP-PP (34) | Ac-IGLHDPSHGTLPNGSC-OH |
| INGAP-PP (35) | H-IGLHDPSHGTLPNGSC-NH2 |
| INGAP-PP (36) | Ac-IGLHDPSHGTLPNGSC-NH2 |
| INGAP-PP (37) | H-IGLHDPSHGTLPNGC-OH |
| INGAP-PP (38) | Ac-IGLHDPSHGTLPNGC-OH |
| INGAP-PP (39) | H-IGLHDPSHGTLPNGC-NH2 |
| INGAP-PP (40) | Ac-IGLHDPSHGTLPNGC-NH2 |
| INGAP-PP (41) | H-IGLHDPSHGTLPAGS-NH2 |
| INGAP-PP (42) | H-IGLHDPSHGTLPAGSC-OH |
| INGAP-PP (43) | Ac-IGLHDPSHGTLPAGSC-OH |
| INGAP-PP (44) | H-IGLHDPSHGTLPAGSC-NH2 |
| INGAP-PP (45) | Ac-IGLHDPSHGTLPAGSC-NH2 |
| INGAP-PP (46) | H-IGLHDPSHGTLPAGC-OH |
| INGAP-PP (47) | Ac-IGLHDPSHGTLPAGC-OH |
| INGAP-PP (48) | H-IGLHDPSHGTLPAGC-NH2 |
| INGAP-PP (49) | Ac-IGLHDPSHGTLPAGC-NH2 |
| INGAP-PP (73) | IGLHDPSHGTLPAG |

TABLE 1-continued

Exemplary INGAP-PP Analogs

| Peptide Name/ SEQ ID NO | Sequence |
| --- | --- |
| INGAP-PP (74) | IGLHDPSHGTLPNG |
| INGAP-PP (75) | Ac-IGLHDPSHGTLPNG |
| INGAP-PP (76) | IGLHDPSHGTLPNG-NH2 |
| INGAP-PP (77) | Ac-IGLHDPSHGTLPNG-NH2 |
| INGAP-PP (78) | H-IGLHDPSHGTLPQGS-OH |
| INGAP-PP (79) | H-IGLHDPSHGTLPDGS-OH |
| INGAP-PP (80) | H-IGLHDPSHGTLPEGS-OH |
| INGAP-PP (81) | H-IGLHEPSHGTLPNGS-OH |
| INGAP-PP (82) | H-IGLHQPSHGTLPNGS-OH |
| INGAP-PP (83) | H-IGLHNPSHGTLPNGS-OH |
| INGAP-PP (84) | H-IGLHEPSHGTLPAGS-OH |
| INGAP-PP (85) | H-IGLHQPSHGTLPAGS-OH |
| INGAP-PP (86) | H-IGLHNPSHGTLPAGS-OH |
| INGAP-PP (87) | H-IGLHDPSHGTLPQGSC-OH |
| INGAP-PP (88) | H-IGLHDPSHGTLPDGSC-OH |
| INGAP-PP (89) | H-IGLHDPSHGTLPEGSC-OH |
| INGAP-PP (90) | H-IGLHEPSHGTLPNGSC-OH |
| INGAP-PP (91) | H-IGLHQPSHGTLPNGSC-OH |
| INGAP-PP (92) | H-IGLHNPSHGTLPNGSC-OH |
| INGAP-PP (93) | H-IGLHDPSHGTLPQG-OH |
| INGAP-PP (94) | H-IGLHDPSHGTLPDG-OH |
| INGAP-PP (95) | H-IGLHDPSHGTLPEG-OH |
| INGAP-PP (96) | H-IGLHEPSHGTLPNG-OH |
| INGAP-PP (97) | H-IGLHQPSHGTLPNG-OH |
| INGAP-PP (98) | H-IGLHNPSHGTLPNG-OH |
| INGAP-PP (99) | H-IGLHEPSHGTLPAG-OH |
| INGAP-PP (100) | H-IGLHQPSHGTLPAG-OH |
| INGAP-PP (101) | H-IGLHNPSHGTLPAG-OH |
| INGAP-PP (102) | H-IGLHDPSHGTLPQGE-OH |
| INGAP-PP (103) | H-IGLHDPSHGTLPDGE-OH |
| INGAP-PP (104) | H-IGLHDPSHGTLPEGE-OH |
| INGAP-PP (105) | H-IGLHEPSHGTLPNGE-OH |
| INGAP-PP (106) | H-IGLHQPSHGTLPNGE-OH |
| INGAP-PP (107) | H-IGLHNPSHGTLPNGE-OH |
| INGAP-PP (108) | H-IGLHEPSHGTLPAGE-OH |
| INGAP-PP (109) | H-IGLHQPSHGTLPAGE-OH |
| INGAP-PP (110) | H-IGLHNPSHGTLPAGE-OH |

TABLE 2

Exemplary HIP Analogs

| Peptide ID/ SEQ ID NO | Sequence |
| --- | --- |
| HIP (2) | H-IGLHDPTQGTEPNGE-OH |
| HIP (50) | H-IGLHDPTQGTEPAGE-OH |
| HIP (51) | H-IGLHDPTQGTEP(Aib)GE-OH |
| HIP (52) | Ac-IGLHDPTQGTEPAGE-OH |
| HIP (53) | H-(D-Isoleucine)GLHDPTQGTEPAGE-OH |
| HIP (54) | Ac-IGLHDPTQGTEPNGE-OH |
| HIP (55) | H-(D-Isoleucine)GLHDPTQGTEPNGE-OH |
| HIP (56) | H-IGLHDPTQGTEPNGS-OH |
| HIP (57) | H-IGLHDPTQGTEPAGS-OH |
| HIP (58) | H-IGLHDPTQGTLPNGE-OH |
| HIP (59) | H-IGLHDPTQGTLPAGE-OH |
| HIP (60) | Ac-IGLHDPTQGTEPAG-NH2 |
| HIP (61) | Ac-IGLHDPTQGTEPNGE-NH2 |
| HIP (62) | Ac-IGLHDPTQGTEPAGE-NH2 |
| HIP (63) | H-IGLHDPTQGTEPNGE-NH2 |
| HIP (64) | H-IGLHDPTQGTEPNGC-OH |
| HIP (65) | Ac-IGLHDPTQGTEPNGC-OH |
| HIP (66) | H-IGLHDPTQGTEPNGC-NH2 |
| HIP (67) | Ac-IGLHDPTQGTEPNGC-NH2 |
| HIP (68) | H-IGLHDPTQGTEPAGE-NH2 |
| HIP (69) | H-IGLHDPTQGTEPAGC-OH |
| HIP (70) | Ac-IGLHDPTQGTEPAGC-OH |
| HIP (71) | H-IGLHDPTQGTEPAGC-NH2 |
| HIP (72) | Ac-IGLHDPTQGTEPAGC-NH2 |

As disclosed herein, the present invention provides fusion peptides combining INGAP-PP or HIP peptides and analogs with GLP-1 receptor agonists, epidermal growth factor receptor agonists, or Cathelicidin antimicrobial peptides or analogs with desirable synergistic pharmaceutical properties for clinical development. The present invention also provides pharmaceutical compositions comprising a compound according to the present invention and the use of compounds according to the present invention for preparing medicaments for treating metabolic diseases, such as type 1 diabetes (T1D) and type 2 diabetes (T2D). The invention further provides the compositions in suitable formulations, including sustained release formulations.

As described previously, a hamster protein was identified that promoted pancreatic islet neogenesis and was termed islet neogenesis associated protein (INGAP). (U.S. Pat. No. 5,834,590.) A pentadecapeptide fragment of INGAP, referred to herein as INGAP-PP, has been described and shown to reverse diabetes in a mouse model. (Rosenberg et al., *Ann. Surg.* 240:875-884 (2004); US publication 2006/0009516; see also US publication 2008/0171704; Kapur et al., *Islets* 4:1-9 (2012); Chang et al., *Mol. Cell. Endocrinol.* 335:104-109 (2011); Borelli et al., *Regulatory Peptides* 131:97-102 (2005); Dungan et al., *Diabetes/Metabolism Res. Rev.* 25:558-565 (2009); Zha et al., *J. Endocrinol. Invest.* 35:634-639 (2012); Wang et al., *J. Cell. Physiol.* 224:501-508 (2010); Petropavlovskaia et al., *J. Endocrinol.* 191:65-81 (2006); Taylor-Fishwick et al., *Pancreas* 39:64-70 (2010); Rosenberg, *Diabetologia* 39:256-262 (1996); Madrid et al., *Regulatory Peptides* 157:25-31 (2009); and Taylor-Fishwick et al., *J. Endocrinol.* 190:729-737 (2006).) A human peptide, termed human proIslet peptide (HIP) has also been described (Levetan et al., *Endocrin. Pract.* 14:1075-1083 (2008); US publication 2011/0280833).

Glucagon-like peptide-1 receptor agonists also known as incretin mimetics. Several drugs in this class have been approved for the treatment of T2D, including exenatide, liraglutide, lixisenatide, albiglutide, and dulaglutide. GLP-1 action has been clearly proven to stimulate insulin secretion, suppress glucagon secretion, inhibit gastric emptying, and reduce appetite and food intake. Clinical trials with incretin mimetics demonstrated reductions in fasting and postprandial glucose concentrations, haemoglobin A1c (HbA1c), and body weight. In animal studies, GLP-1 receptor agonists have been reported to enhance beta-cell mass by proliferative effects, however, this has not been approved in clinics since the use of GLP-1 receptor agonists in T1D failed to demonstrate any capacity of pancreatic beta-cell regeneration. Nevertheless, they may be useful for preserving remaining beta cells in diabetes.

Epidermal growth factor (EGF) is a growth factor that stimulates cell growth, proliferation, and differentiation by binding to its receptor EGFR. Human EGF is a polypeptide with 53 amino acid residues. Previously, the combination therapy of EGF and gastrin was attempted to increase beta-cell mass and reverse hyperglycemia in diabetes with limited success, further investigation is warranted.

Cathelicidin antimicrobial peptide (CAMP) is a naturally occurring secreted peptide that is expressed in several organs with pleiotropic roles in immunomodulation, wound healing, and cell growth. CAMP expression in the pancreatic β-cells of rat, mouse, and human has been demonstrated in previous studies. CAMP treatment promoted insulin and glucagon secretion from isolated rat islets. Daily treatment with the CAMP/LL-37 peptide in vivo in BBdp rats resulted in enhanced β-cell neogenesis and upregulation of potentially beneficial gut microbes. Therefore, CAMP is considered a promoter of islet paracrine signaling that enhances islet function and glucoregulation.

As an indispensable component of fusion proteins/peptides, a linker plays instrumental roles in the construction of stable, bioactive fusion proteins/peptides. Empirical linkers are generally classified into 3 categories according to their structures: flexible linkers, rigid linkers, and in vivo cleavable linkers. Besides the basic role in linking the functional domains together (as in flexible and rigid linkers) or releasing free functional domain in vivo (as in in vivo cleavable linkers), linkers offer many other advantages for the production of fusion proteins/peptides, such as improving biological activity, increasing expression yield, and achieving desirable pharmacokinetic profiles. For example, many protein drugs are fused to Fc domains of antibodies, such as Fc-immunoglobulin G1 (Fc-IgG1), or to carrier proteins such as human serum albumin (HSA) or transferrin (Tf) to extend their plasma half-lives and to achieve enhanced therapeutic effects. They have also been widely applied for drug targeting, since proteins such as single chain antibodies or ligands for cell surface receptors can specifically target a linked functional protein (e.g., toxin or cytokine) to a specific type of cells. In drug delivery, the combination of protein drugs to carrier moieties such as cell penetrating peptides, antibodies or Tf can achieve efficient transport of the protein drugs across biological barriers such as cell membranes, the blood brain barrier or intestinal epithelium. Several fusion proteins drugs including Enbrel® (tumor necrosis factor/Fc-IgG1), Ontak® (Interleukin-2/diphtheria toxin), Orencia® (Cytotoxic T-Lymphocyte Antigen-4/Fc-IgG1), Amevive® (Leukocyte function antigen-3/Fc-IgG1), Arcalyst® (Interleukin-1 Receptor extracellular domain/Fc-IgG1), and Nplate® (thrombopoietin/Fc-IgG1) have been approved by the FDA.

Fc-fusion is an effective method to link two active moieties. Several Fc-fusion based drugs have been approved by FDA, and the advantages of Fc-fusion drugs over other types of biopharmaceuticals have been well recognized.

The present invention provides INGAP-PP or HIP peptides and analogs conjugated with GLP-1 receptor agonists, epidermal growth factor receptor agonists, or Cathelicidin antimicrobial peptides or analogs via a suitable linker:

1) INGAP-PP or HIP and analogs+linker+GLP-1 receptor agonist

2) INGAP-PP or HIP and analogs+linker+epidermal growth factor receptor agonist

3) INGAP-PP or HIP and analogs+linker+Cathelicidin antimicrobial peptide or analogs 4) GLP-1 receptor agonist+linker+INGAP-PP or HIP analogs 5) Epidermal growth factor receptor agonist+linker+INGAP-PP or HIP analogs 6) Cathelicidin antimicrobial peptide or analogs+linker+INGAP-PP or HIP analogs The linker can be either flexible or rigid linkers derived from naturally-occurring multi-domain proteins, such as $(GGGGS)_n$ (n=1-4) (SEQ ID NO: 121), $(EAAAK)_n$ (n=1-3) (SEQ ID NO: 122), $(Gly)_n$ (n=6-8) (SEQ ID NO: 123), $A(EAAAK)_4ALEA(EAAAK)_4A$ (SEQ ID NO: 124), just to name a few; these linkers covalently join functional domains together to act as one molecule throughout the in vivo processes. The stable linkage between functional domains provides many advantages such as a prolonged plasma half-life (e.g., albumin or Fc-fusions). The linker can also be in vivo cleavable linkers, such as linkers that can be cleaved under specific conditions, for example, in the presence of reducing reagents or proteases to free functional domains in vivo. This type of linker may reduce steric hindrance, improve bioactivity, or achieve independent actions/metabolism of individual domains of recombinant fusion proteins after linker cleavage.

As used herein, the term "peptide" refers to a polymer of two or more amino acids. The peptide can be modified to include analogs, derivatives, functional mimetics, pseudo-peptides, and the like, so long as the peptide comprises a polymer of at least two amino acids. The meaning of the term "peptide" is well known to those skilled in the art. In general, a peptide includes two or more amino acids joined by an amide bond between the carboxyl group of one amino acid residue and the amino group of the adjacent amino acid residue. As described herein, a peptide can comprise naturally occurring amino acids or non-naturally occurring amino acids.

As used herein, the term "analog" refers to a variant of a parent molecule, for example, a parent peptide. For example, an analog of a parent peptide can include a variant, where one or more amino acids are substituted relative to the parent peptide. An analog can also include a modification of a parent peptide, including but not limited to, non-naturally occurring amino acids, D amino acids, modified amino- and/or carboxy-terminal (N- or C-terminal) amino acids, in particular modifications of the amino group on the N-terminus and/or modification of the carboxyl group in the C-terminus, fatty acid modifications, esterification, peptidomimetics, pseudopeptides, and the like, as disclosed herein. Exemplary modifications are described in more details below.

As used herein, the phrase "impaired pancreatic function" refers to a disease or condition associated with the pancreas, where the pancreas exhibits a decreased function compared to that of a normal or healthy individual. Exemplary diseases or conditions associated with impaired pancreatic function include, but are not limited to, type 1 diabetes, type 2 diabetes, latent autoimmune diabetes in adults (LADA), impaired fasting glucose, impaired glucose tolerance, insulin deficiency, fasting hyperinsulinemia, insulin resistance, impaired fasting insulin levels, partial pancreatomy due to injury or inflammation, or a combination thereof.

As described herein, the invention provides peptide analogs of INGAP-PP or HIP peptides conjugated with GLP-1 receptor agonists, epidermal growth factor receptor agonists, or Cathelicidin antimicrobial peptides (CAMP) or analogs.

TABLE 3

Exemplary Sequences

| Code | SEQ ID NO: | Sequence |
|---|---|---|
| Peptide 1 | 111 | HGEGT FTSDL SKQME EEAVR LFIEW LKNGG GGSIG LHDPS HGTLP NGS-NH2 |
| Peptide 2 | 112 | HGEGT FTSDL SKQME EEAVR LFIEW LKNAE AAAKI GLHDP SHGTL PNGS-NH2 |
| Peptide 3 | 113 | HGEGT FTSDL SKQME EEAVR LFIEW LKNGG GGSIW IGLHD PSHGT LPNGS-NH2 |
| Peptide 4 | 114 | IGLHD PSHGT LPAGS GGGGS HGEGT FTSDL SKQME EEAVR LFIEW LKN |
| Peptide 5 | 115 | IGLHD PSHGT LPAGS GGGGG GHGEG TFTSD LSKQM EEEAV RLFIE WLKN |
| Peptide 6 | 116 | IGLHD PSHGT LPAGS AEAAA KHGEG TFTSD LSKQM EEEAV RLFIE WLKN |
| Peptide 7 | 117 | LLGDF FRKSK EKIGK EFKRI VQRIK DFLRN LVPRT ESGGG GSIGL HDPSH GTLPN GS-NH2 |
| Peptide 8 | 118 | LLGDF FRKSK EKIGK EFKRI VQRIK DFLRN LVPRT ESAEA AAKIG LHDPS HGTLP NGS-NH2 |

TABLE 3-continued

Exemplary Sequences

| Code | SEQ ID NO: | Sequence |
|---|---|---|
| Peptide 9 | 119 | IGLHD PSHGT LPAGS GGGGS LLGDF FRKSK EKIGK EFKRI VQRIK DFLRN LVPRT ES |
| Peptide 10 | 120 | IGLHD PSHGT LPAGS AEAAA KLLGD FFRKS KEKIG KEFKR IVQRI KDFLR NLVPR TES |

As described herein, examples of linkers are presented in Table 4.

TABLE 4

Examples of linkers

| Linker Type | SEQ ID NO: | Sequence |
|---|---|---|
| Flexible | 121 | $(GGGGS)_n$ $(n=1-4)$ |
|  | 125 | $(Gly)_8$ |
|  | 126 | $(Gly)_6$ |
| Rigid | 122 | $(EAAAK)_n$ $(n=1-3)$ |
|  | 124 | $A(EAAAK)_4ALEA(EAAAK)_4A$ |
|  | 127 | AEAAAKEAAAKA |
|  | 128 | PAPAP |
|  | 129 | (Ala-Pro)n (n = 5-17) |
| Cleavable |  | Cys-Cys disulfide |
|  | 130 | VSQTSKLTR↓AETVFPDV |
|  | 131 | PLG↓LWA |
|  | 132 | TRHRQPR↓GWE |

In one aspect, the invention generally relates to a compound having the formula of (I):

X-L-Y            (I)

wherein X is selected from INGAP-PP or an analog thereof, or HIP or an analog thereof; L is a linker covalently bonded to X; and Y is a GLP-1 receptor agonist.

In another aspect, the invention generally relates to a compound having the formula of (II):

X-L-Y            (II)

wherein X is selected from INGAP-PP or an analog thereof, or HIP or an analog thereof; L is a linker covalently bonded to X; and Y is an epidermal growth factor receptor agonist.

In yet another aspect, the invention generally relates to a compound having the formula of (III):

X-L-Y            (III)

wherein X is selected from INGAP-PP or an analog thereof, or HIP or an analog thereof; L is a linker covalently bonded to X; and Y is a cathelicidin antimicrobial peptide or an analog thereof.

In yet another aspect, the invention generally relates to a compound having the formula of (IV):

Y-L-X    (IV)

wherein X is selected from INGAP-PP or an analog thereof, or HIP or an analog thereof; L is a linker covalently bonded to X; and Y is a GLP-1 receptor agonist.

In yet another aspect, the invention generally relates to a compound having the formula of (V):

Y-L-X    (V)

wherein X is selected from INGAP-PP or an analog thereof, or HIP or an analog thereof; L is a linker covalently bonded to X; and Y is an epidermal growth factor receptor agonist.

In yet another aspect, the invention generally relates to a compound having the formula of (VI):

Y-L-X    (VI)

wherein X is selected from INGAP-PP or an analog thereof, or HIP or an analog thereof; L is a linker covalently bonded to X; and Y is a cathelicidin antimicrobial peptide or an analog thereof.

Any suitable linker L may be used. In certain embodiments, L is a flexible linker. In certain embodiments, L is a rigid linker. In certain embodiments, L is an in vivo cleavable linker. In certain embodiments, L is a linker comprising a Fc domain of an antibody. In certain embodiments, L is a linker comprising Fc-IgG1.

In yet another aspect, the invention generally relates to a compound comprising the sequence of:

(SEQ ID NO: 111)
HGEGT FTSDL SKQME EEAVR LFIEW LKNGG GGSIG LHDPS

HGTLP NGS-NH2.

In yet another aspect, the invention generally relates to a compound comprising the sequence of:

(SEQ ID NO: 112)
HGEGT FTSDL SKQME EEAVR LFIEW LKNAE AAAKI GLHDP

SHGTL PNGS-NH2.

In yet another aspect, the invention generally relates to a compound comprising the sequence of:

(SEQ ID NO: 113)
HGEGT FTSDL SKQME EEAVR LFIEW LKNGG GGSIW IGLHD

PSHGT LPNGS-NH2.

In yet another aspect, the invention generally relates to a compound comprising the sequence of:

(SEQ ID NO: 114)
IGLHD PSHGT LPAGS GGGGS HGEGT FTSDL SKQME EEAVR

LFIEW LKN.

In yet another aspect, the invention generally relates to a compound comprising the sequence of:

(SEQ ID NO: 115)
IGLHD PSHGT LPAGS GGGGG GHGEG TFTSD LSKQM EEEAV

RLFIE WLKN.

In yet another aspect, the invention generally relates to a compound comprising the sequence of:

(SEQ ID NO: 116)
IGLHD PSHGT LPAGS AEAAA KHGEG TFTSD LSKQM EEEAV

RLFIE WLKN.

In yet another aspect, the invention generally relates to a compound comprising the sequence of:

(SEQ ID NO: 117)
LLGDF FRKSK EKIGK EFKRI VQRIK DFLRN LVPRT ESGGG

GSIGL HDPSH GTLPN GS-NH2.

In yet another aspect, the invention generally relates to a compound comprising the sequence of:

(SEQ ID NO: 118)
LLGDF FRKSK EKIGK EFKRI VQRIK DFLRN LVPRT ESAEA

AAKIG LHDPS HGTLP NGS-NH2.

In yet another aspect, the invention generally relates to a compound comprising the sequence of:

(SEQ ID NO: 119)
IGLHD PSHGT LPAGS GGGGS LLGDF FRKSK EKIGK EFKRI

VQRIK DFLRN LVPRT ES.

In yet another aspect, the invention generally relates to a compound comprising the sequence of:

(SEQ ID NO: 120)
IGLHD PSHGT LPAGS AEAAA KLLGD FFRKS KEKIG KEFKR

IVQRI KDFLR NLVPR TES.

In yet another aspect, the invention generally relates to a composition comprising a compound disclosed herein.

In certain embodiments, the composition is a pharmaceutical composition comprising a pharmaceutically acceptable carrier suitable for therapeutic use.

In certain embodiments, the composition is useful for treating impaired pancreatic function, treating a metabolic disease, promoting neuroprotection or nerve regeneration, promoting liver regeneration or inhibiting inflammation.

In yet another aspect, the invention generally relates to a method for ameliorating a sign or symptom associated with impaired pancreatic function. The method includes administering a compound disclosed herein.

In certain embodiments of the method, the impaired pancreatic function is type 1 diabetes, type 2 diabetes, latent autoimmune diabetes in adults (LADA), impaired fasting glucose, impaired glucose tolerance, insulin deficiency, fasting hyperinsulinemia, insulin resistance, or impaired fasting insulin level, or a combination thereof.

In certain embodiments of the method, an anti-diabetic drug is administered.

In yet another aspect, the invention generally relates to a method for stimulating pancreatic islet cell growth. The method includes contacting a pancreatic islet cell with a compound disclosed herein, whereby proliferation of the pancreatic islet cell is stimulated.

In yet another aspect, the invention generally relates to a method of producing a population of pancreatic islet cells.

The method includes contacting one or more pancreatic islet cells in vitro with a compound disclosed herein, whereby proliferation of the one or more pancreatic islet cells are stimulated and a population of pancreatic islet cells is produced.

In certain embodiments of the method, the one or more pancreatic islet cells are obtained from a subject.

In certain embodiments, the method further includes the step of transplanting the population of pancreatic islet cells into a subject.

In certain embodiments of the method, the one or more pancreatic cells are obtained from the subject into which the population of pancreatic islet cells is to be transplanted.

In yet another aspect, the invention generally relates to a method for increasing the number of pancreatic islet cells in a subject. The method includes administering a compound disclosed herein.

In yet another aspect, the invention generally relates to a method for ameliorating a sign or symptom associated with a metabolic disease in a subject. The method includes administering a compound disclosed herein.

In certain embodiments of the method, the metabolic disease is diabetes, pre-diabetes or metabolic syndrome.

In yet another aspect, the invention generally relates to a method of reducing in a diabetic subject impaired glucose tolerance, blood glucose, fasting blood glucose, postprandial blood glucose, insulin deficiency, fasting hyperinsulinemia, insulin resistance, impaired fasting insulin levels, glycosylated hemoglobin (HbA1c), arginine-stimulated C-peptide (AUC), or a combination thereof. The method includes administering a compound disclosed herein.

In yet another aspect, the invention generally relates to a method for promoting neuroprotection or nerve regeneration, comprising contacting a nerve cell with a compound disclosed herein.

In yet another aspect, the invention generally relates to a method for promoting liver regeneration, comprising contacting a liver cell with a compound disclosed herein.

In certain embodiments of the method, the contacting occurs in vitro. In certain embodiments of the method, the contacting occurs in vivo.

In yet another aspect, the invention generally relates to a method for inhibiting inflammation, comprising administering a compound disclosed herein.

As described herein, the compounds and analogs of the invention exhibit unexpected properties compared to that of INGAP-PP/HIP peptide (including the peptides and analogs of Tables 1 and 2) or GLP-1 receptor agonists/epidermal growth factor receptor agonists/Cathelicidin antimicrobial peptides (CAMP) or analogs used alone. As disclosed herein, compounds and analogs of the invention exhibit a significantly increased ability to stimulate insulin secretion in primary pancreatic islet cells (see Example II). Additionally, peptide analogs of the invention exhibited superior effect at improving blood glucose and oral glucose tolerance (see Example III). The numerous unexpected and superior properties of the compounds and analogs of the invention indicate that the compound and analogs of the invention, including the compound and analogs of Table 3, can be utilized for therapeutic applications. The compounds and analogs of the invention exhibit greater potency than that of INGAP-PP/HIP peptide (including the peptides and analogs of Tables 1 and 2) or GLP-1 receptor agonists/epidermal growth factor receptor agonists/Cathelicidin antimicrobial peptides (CAMP) or analogs used alone.

It is understood that modifications which do not substantially affect the activity of the various embodiments of this invention are also provided within the definition of the invention provided herein. Accordingly, the following examples are intended to illustrate but not limit the present invention.

Example I

Production of Peptides and Peptide Analogs

This example describes the production of peptides and peptide analogs.

All the peptides used in the studies were synthesized by solid phase peptide synthesis using 9-fluorenylmethoxy carbonyl (Fmoc) chemistry. In brief, a pre-weighed amount of 2-chlorotrityl chloride resin (1.6 mmol/g) was swelled in dichloromethane (DCM). For peptides with an amidated C-terminus, Rink amide resin was used instead of 2-chlorotrityl chloride resin. Fmoc-preactivated amino acids were used for the coupling reactions in the presence of hydroxybenzotriazole (Sigma Chemical Co., St. Louis, Mo., USA) in dimethylformamide (DMF). Excess amino acids were used throughout the synthesis. Chain elongation reaction was performed followed by Fmoc deprotection in 20% piperidine in DMF. When the chain elongation reaction was finished, the Fmoc protecting groups were removed from the N terminus of the peptides by 25% piperidine in DMF followed by washing with DMF for four times. For peptides with an acetylated N-terminus, before trifluoroacetic acid (TFA) cleavage, a solution of 20% acetic anhydride dissolved in DMF was added at a ratio of 7 mL/g resin, reacted for 30 mins, followed by 4 times washes with DMF and DCM. Following washing for four times with DMF and DCM, the resin was dried under vacuum. Subsequently, the prepared peptides were cleaved from the resin using standard TFA cleavage procedures in TFA with 5% $H_2O$ followed by multiple ether extractions. All synthetic peptides were purified to >95% by reverse-phase high-pressure liquid chromatography performed with a liquid chromatograph. Peptides were analyzed by mass spectrometry to confirm the identity and purity.

For ex-vivo studies, the above prepared peptides were dissolved in double distilled water to make a stock solution, and in the in vivo efficacy study they were reconstituted in sterile normal saline to reach the desired concentration. The final peptide solution was filtered through a 0.22 μm membrane to make it sterile.

The peptides and analogs can also be produced using other well-known methods, including manufacturing the peptides using a method of peptide synthesis or expressing nucleic acids that code for the desired peptides or peptide analogs. Thus, when the analogs include one or more non-standard amino acids, it is more likely that they will be produced by a chemical synthetic method. When the peptides include only one or more substitutions with standard amino acids, the peptides can be expressed from an expression vector using well known expression methods.

The particular peptides used in the experiments below can be found in Table 3, the HPLC chromatograms and MS spectrums of Peptide 1, Peptide 2, and Peptide 3 were shown in FIGS. 1-3. The linker for the three peptides are "GGGGS" (SEQ ID NO: 133), "AEAAAK" (SEQ ID NO: 134) and "GGGGS" (SEQ ID NO: 133) respectively, for whichever peptide shown in Table 3, the sequence in front of the linker is an exemplary GLP-1 receptor agonist and the sequence after the linker is an exemplary INGAP-PP or HIP analog. Additional exemplary peptides are also listed in Table 3.

Example II

The Effect of Peptides on Glucose-Stimulated Insulin Secretion

This example describes the effect of peptides on glucose-stimulated insulin secretion (GSIS).

The pancreases were procured from male adult C57BL/6J mice. After 7 days acclimation, the animals were sacrificed by cervical dislocation and the entire pancreas was removed and digested with collagenase to isolate islets. After digestion, islets were maintained at 37° C. in RPMI 1640 (Carlsbad Calif., USA) pH 7.4, containing 10% (v/v) fetal calf serum, 1% penicillin/streptomycin, and 10 mM glucose in a humid atmosphere (5% $CO_2$/95% $O_2$), without the addition of any compound (control), or with the addition of 10 nM glucagon like peptide-1 (GLP-1); or 10 nM INGAP-PP; or 10 nM Peptide 1, Peptide 2 or Peptide 3, as summarized in Table 5 below.

TABLE 5

Parameters for Various Groups Tested for Glucose-stimulated Insulin Secretion (GSIS)

| | 1 | 2 | 3 | 4 | 5 | 6 | 7 |
|---|---|---|---|---|---|---|---|
| A | 2.8 mM Glucose | 16.7 mM Glucose | 16.7 mM Glucose; 10 nM GLP-1 | 16.7 mM Glucose; 10 nM INGAP-PP | 16.7 mM Glucose; 10 nM Peptide 1 | 16.7 mM Glucose; 10 nM Peptide 2 | 16.7 mM Glucose; 10 nM Peptide 3 |
| B | 2.8 mM Glucose | 16.7 mM Glucose | 16.7 mM Glucose; 10 nM GLP-1 | 16.7 mM Glucose; 10 nM INGAP-PP | 16.7 mM Glucose; 10 nM Peptide 1 | 16.7 mM Glucose; 10 nM Peptide 2 | 16.7 mM Glucose; 10 nM Peptide 3 |
| C | 2.8 mM Glucose | 16.7 mM Glucose | 16.7 mM Glucose; 10 nM GLP-1 | 16.7 mM Glucose; 10 nM INGAP-PP | 16.7 mM Glucose; 10 nM Peptide 1 | 16.7 mM Glucose; 10 nM Peptide 2 | 16.7 mM Glucose; 10 nM Peptide 3 |
| D | 2.8 mM Glucose | 16.7 mM Glucose | 16.7 mM Glucose; 10 nM GLP-1 | 16.7 mM Glucose; 10 nM INGAP-PP | 16.7 mM Glucose; 10 nM Peptide 1 | 16.7 mM Glucose; 10 nM Peptide 2 | 16.7 mM Glucose; 10 nM Peptide 3 |

Cultured islets were rinsed in Krebs-Ringer bicarbonate buffer (KRB), pH 7.4, previously gassed with a mixture of $CO_2/O_2$ (5/95%), and pre-incubated in 1.0 mL of KRB containing 0.5% (w/v) BSA and 2.8 mM glucose at 37° C. for 45 min. After this period, groups of 5 islets were incubated in 0.6 mL KRB with the addition of 2.8 or 16.7 mM glucose, with or without the addition of peptides for 60 min. At the end of the incubation period, aliquots of the medium were collected for insulin quantitation.

The results of the insulin quantitation are shown in Table 6. The results show the increase of glucose-stimulated insulin secretion of islets with or without the co-incubation of 10 nM peptides, Peptide 1, Peptide 2 and Peptide 3. Co-incubation with 10 nM Glucagon like peptide-1 (GLP-1) or INGAP-PP was also included. At 16.7 mM glucose concentration, pancreatic islets cultured with peptides GLP-1, Peptide 1, Peptide 2 or Peptide 3 released significantly more insulin than those cultured without the addition of peptides, and no stimulation was observed with the addition of INGAP-PP. In particular, Peptide 1, Peptide 2 or Peptide 3 showed higher stimulation of insulin secretion than GLP-1 used alone.

These results demonstrate that fusion peptide analogs stimulated insulin secretion from pancreatic islet cells, and higher stimulation of insulin secretion than GLP-1 or INGAP-PP used alone was verified.

TABLE 6

The Glucose Stimulated Insulin Secretion Results

| Group | Insulin Secretion ng/islet/hour |
|---|---|
| 2.8 mM Glucose | 0.38 ± 0.12 |
| 16.7 mM Glucose | 2.3 ± 0.8 ** |
| 16.7 mM Glucose + 10 nM GLP-1 | 5.4 ± 2.1 ## |
| 16.7 mM Glucose + 10 nM INGAP-PP | 2.5 ± 1.0 # |
| 16.7 mM Glucose + 10 nM Peptide 1 | 7.2 ± 3.1 && |
| 16.7 mM Glucose + 10 nM Peptide2 | 12.8 ± 4.2 $, &&& |
| 16.7 mM Glucose + 10 nM Peptide3 | 10.6 ± 3.9 $, &&& |

\** $P < 0.01$ vs. 2.8 mM;
\## $P < 0.01$ vs. 16.7 mM;
$ $P < 0.05$ vs. 16.7 mM + 10 nM GLP-1;
$$ $P < 0.01$ vs. 16.7 mM + 10 nM GLP-1;
&& $P < 0.01$ vs. 16.7 mM + 10 nM INGAP-PP;
&&& $P < 0.001$ vs. 16.7 mM + 10 nM INGAP-PP

Example III

Efficacy of Peptide Analogs in a Diabetic Mouse Model

This example describes an in vivo efficacy study using a streptozotocin (STZ) induced diabetic mice model.

After acclimatization in the animal facility for one week, 6-8 weeks old C57BL/6J mice were administered high dose STZ at 150 mg/kg in citrate buffer to establish a T1D animal model. Mice with blood glucose greater than 16.7 mmol/L at 10 days post last STZ injection were included in the study. These mice were then treated with INGAP-PP or GLP-1 or Peptide 2 at the dose of 250 nM/kg for 10 days before sacrifices. One additional group of diabetic mice were administered with saline as model control groups. Blood glucose levels were measured on day 8. Ten days post the last dosing of test agents, an oral glucose tolerance test (OGTT) was performed in 6 hours fasted animals. Blood samples obtained from the tail for glucose determination were detected with an ACCU-CHEK™ glucometer (Roche, ACCU-CHEK® Performa)

TABLE 7

The Blood Glucose and AUC of OGTT Results

| | Normal Control | Model Control | Model + GLP-1 | Model + INGAP-PP | Model + Peptide2 |
|---|---|---|---|---|---|
| Blood Glucose (mM) (Day 8) | 8.3 ± 1.2 | 27.9 ± 8.7 | 22.1 ± 6.8 | 25.9 ± 9.1 | 18.6 ± 5.3 |
| AUC of OGTT (Day 10) | 1980.2 ± 318.4 | 3351.5 ± 793.4 | 3054.7 ± 728.9 | 3207.6 ± 801.5 | 2512.3 ± 571.8 |

Table 7 shows the efficacy comparison of GLP-1, INGAP-PP, INGAP and Peptide 2 in STZ induced diabetic mice model. The blood glucose (BG, mM) present were measured on day 8 of treatment. The area under curve (AUC) of glucose ($T_{0\sim120\ min}$) measured in an oral glucose tolerance test (OGTT) on day 10 of treatment.

Significant differences in blood glucose levels were observed between the mouse group administered Peptide 2 and the saline control group. Moreover, the blood glucose levels of the Peptide 2 treated animals were lower than the GLP-1 and INGAP-PP treated groups. In addition, the Peptide 2 treated group also showed the most improved glucose tolerance.

These results demonstrate that a representative fusion peptide analog, peptide 2, was effective at ameliorating signs and symptoms of diabetes in a diabetic mouse model and the effect was more profound than GLP-1 or INGAP-PP used alone.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples disclosed herein are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance that can be adapted to the practice of this invention in its various embodiments and equivalents thereof.

What is claimed is:

1. A compound having the formula of (I):

X-L-Y    (I)

wherein
   X is selected from islet neogenesis-associated protein peptide (INGAP-PP) or an analog thereof, or human proIslet peptide (HIP) or an analog thereof;
   L is a linker selected from (EAAAK)$_m$, wherein m is 1, 2 or 3 (SEQ ID NO: 122), A(EAAAK)$_4$ALEA(EAAAK)$_4$A (SEQ ID NO: 124), AEAAAKEAAAKA (SEQ ID NO: 127), PAPAP (SEQ ID NO: 128) and (AP)$_n$, wherein n is an integer selected from 5-17 (SEQ ID NO: 129); and
   Y is an epidermal growth factor receptor agonist or a cathelicidin antimicrobial peptide, or an analog thereof.

2. The compound of claim 1, wherein L is (EAAAK)$_m$, wherein m is 1, 2 or 3 (SEQ ID NO: 122).

3. The compound of claim 1, wherein L is A(EAAAK)$_4$ALEA(EAAAK)$_4$A (SEQ ID NO: 124).

4. The compound of claim 1, wherein L is AEAAAKEAAAKA (SEQ ID NO: 127).

5. The compound of claim 1, wherein L is PAPAP (SEQ ID NO: 128).

6. The compound of claim 5, wherein L is (AP)$_n$, wherein n is an integer selected from 5-17 (SEQ ID NO: 129).

7. A pharmaceutical composition comprising a compound of claim 1 and a pharmaceutically acceptable carrier.

8. The compound of claim 1, wherein Y is an epidermal growth factor receptor agonist.

9. The compound of claim 1, wherein Y is a cathelicidin antimicrobial peptide.

* * * * *

SEQUENCE LISTING

<160> NUMBER OF SEQ ID NOS: 134

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ile Gly Leu His Asp Pro Ser His Gly Thr Leu Pro Asn Gly Ser
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ile Gly Leu His Asp Pro Thr Gln Gly Thr Glu Pro Asn Gly Glu
1               5                   10                  15

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Gly Leu His Ala Pro Ser His Gly Thr Leu Pro Asn Gly Ser
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Gly Leu His Asp Pro Ser His Gly Thr Leu Pro Ala Gly Ser
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Gly Leu His Ala Pro Ser His Gly Thr Leu Pro Ala Gly Ser
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Gly Leu His Asp Pro Ser His Gly Thr Leu Pro Ala Gly Ser Lys
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Aib

<400> SEQUENCE: 10

Ile Gly Leu His Asp Pro Ser His Gly Thr Leu Pro Xaa Gly Ser
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: N-methyl-L-Alanine

<400> SEQUENCE: 11

Ile Gly Leu His Asp Pro Ser His Gly Thr Leu Pro Ala Gly Ser
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Gly Leu His Asp Pro Ser His Gly Thr Leu Pro Ala Gly Ser
1               5                   10                  15

```
<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Isoleucine

<400> SEQUENCE: 13

Ile Gly Leu His Asp Pro Ser His Gly Thr Leu Pro Ala Gly Ser
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-NorValine

<400> SEQUENCE: 14

Val Gly Leu His Asp Pro Ser His Gly Thr Leu Pro Ala Gly Ser
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-NorLeucine

<400> SEQUENCE: 15

Leu Gly Leu His Asp Pro Ser His Gly Thr Leu Pro Ala Gly Ser
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ile Gly Leu His Asp Pro Ser His Gly Thr Leu Pro Asn Gly Ser
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Isoleucine
```

```
<400> SEQUENCE: 17

Ile Gly Leu His Asp Pro Ser His Gly Thr Leu Pro Asn Gly Ser
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ile Gly Leu His Asp Pro Ser His Gly Thr Glu Pro Asn Gly Ser
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ile Gly Leu His Asp Pro Ser Gln Gly Thr Leu Pro Asn Gly Ser
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Gly Leu His Asp Pro Thr His Gly Thr Leu Pro Asn Gly Ser
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ile Gly Leu His Asp Pro Ser His Gly Thr Leu Pro Asn Gly Glu
1               5                   10                  15

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ile Gly Leu His Asp Pro Ser His Gly Thr Leu Pro Asn Gly Lys
1               5                   10                  15

<210> SEQ ID NO 23
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ile Gly Leu His Asp Pro Ser His Gly Thr Leu Pro Ala Gly Lys
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Gly Leu His Asp Pro Ser His Gly Thr Glu Pro Ala Gly Ser
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ile Gly Leu His Asp Pro Ser Gln Gly Thr Leu Pro Ala Gly Ser
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Gly Leu His Asp Pro Thr His Gly Thr Leu Pro Ala Gly Ser
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ile Gly Leu His Asp Pro Ser His Gly Thr Leu Pro Ala Gly Glu
1               5                   10                  15

<210> SEQ ID NO 28
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ile Gly Leu His Asp Pro Ser His Gly Thr Leu Pro Ala Gly
```

<210> SEQ ID NO 29
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ile Gly Leu His Asp Pro Ser His Gly Thr Leu Pro Ala Gly Ser
1               5                   10                  15

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Gly Leu His Asp Pro Ser His Gly Thr Leu Pro Ala Gly
1               5                   10

<210> SEQ ID NO 31
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ile Gly Leu His Asp Pro Ser His Gly Thr Leu Pro Asn Gly Ser
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ile Gly Leu His Asp Pro Ser His Gly Thr Leu Pro Asn Gly Ser
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ile Gly Leu His Asp Pro Ser His Gly Thr Leu Pro Asn Gly Ser Cys
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Ile Gly Leu His Asp Pro Ser His Gly Thr Leu Pro Asn Gly Ser Cys
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ile Gly Leu His Asp Pro Ser His Gly Thr Leu Pro Asn Gly Ser Cys
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ile Gly Leu His Asp Pro Ser His Gly Thr Leu Pro Asn Gly Ser Cys
1               5                   10                  15

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ile Gly Leu His Asp Pro Ser His Gly Thr Leu Pro Asn Gly Cys
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Gly Leu His Asp Pro Ser His Gly Thr Leu Pro Asn Gly Cys
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ile Gly Leu His Asp Pro Ser His Gly Thr Leu Pro Asn Gly Cys
1               5                   10                  15

<210> SEQ ID NO 40

```
<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ile Gly Leu His Asp Pro Ser His Gly Thr Leu Pro Asn Gly Cys
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Gly Leu His Asp Pro Ser His Gly Thr Leu Pro Ala Gly Ser
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ile Gly Leu His Asp Pro Ser His Gly Thr Leu Pro Ala Gly Ser Cys
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ile Gly Leu His Asp Pro Ser His Gly Thr Leu Pro Ala Gly Ser Cys
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Gly Leu His Asp Pro Ser His Gly Thr Leu Pro Ala Gly Ser Cys
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45
```

```
Ile Gly Leu His Asp Pro Ser His Gly Thr Leu Pro Ala Gly Ser Cys
1               5                   10                  15
```

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Ile Gly Leu His Asp Pro Ser His Gly Thr Leu Pro Ala Gly Cys
1               5                   10                  15
```

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

```
Ile Gly Leu His Asp Pro Ser His Gly Thr Leu Pro Ala Gly Cys
1               5                   10                  15
```

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

```
Ile Gly Leu His Asp Pro Ser His Gly Thr Leu Pro Ala Gly Cys
1               5                   10                  15
```

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

```
Ile Gly Leu His Asp Pro Ser His Gly Thr Leu Pro Ala Gly Cys
1               5                   10                  15
```

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

```
Ile Gly Leu His Asp Pro Thr Gln Gly Thr Glu Pro Ala Gly Glu
1               5                   10                  15
```

<210> SEQ ID NO 51
<211> LENGTH: 15
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Aib

<400> SEQUENCE: 51

Ile Gly Leu His Asp Pro Thr Gln Gly Thr Glu Pro Xaa Gly Glu
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ile Gly Leu His Asp Pro Thr Gln Gly Thr Glu Pro Ala Gly Glu
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Isoleucine

<400> SEQUENCE: 53

Ile Gly Leu His Asp Pro Thr Gln Gly Thr Glu Pro Ala Gly Glu
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ile Gly Leu His Asp Pro Thr Gln Gly Thr Glu Pro Asn Gly Glu
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Isoleucine

<400> SEQUENCE: 55

Ile Gly Leu His Asp Pro Thr Gln Gly Thr Glu Pro Asn Gly Glu
1               5                   10                  15

<210> SEQ ID NO 56
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ile Gly Leu His Asp Pro Thr Gln Gly Thr Glu Pro Asn Gly Ser
1               5                   10                  15

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ile Gly Leu His Asp Pro Thr Gln Gly Thr Glu Pro Ala Gly Ser
1               5                   10                  15

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ile Gly Leu His Asp Pro Thr Gln Gly Thr Leu Pro Asn Gly Glu
1               5                   10                  15

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ile Gly Leu His Asp Pro Thr Gln Gly Thr Leu Pro Ala Gly Glu
1               5                   10                  15

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Ile Gly Leu His Asp Pro Thr Gln Gly Thr Glu Pro Ala Gly
1               5                   10

<210> SEQ ID NO 61
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ile Gly Leu His Asp Pro Thr Gln Gly Thr Glu Pro Asn Gly Glu
```

```
1               5                   10                  15
```

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
Ile Gly Leu His Asp Pro Thr Gln Gly Thr Glu Pro Ala Gly Glu
1               5                   10                  15
```

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Ile Gly Leu His Asp Pro Thr Gln Gly Thr Glu Pro Asn Gly Glu
1               5                   10                  15
```

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

```
Ile Gly Leu His Asp Pro Thr Gln Gly Thr Glu Pro Asn Gly Cys
1               5                   10                  15
```

<210> SEQ ID NO 65
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

```
Ile Gly Leu His Asp Pro Thr Gln Gly Thr Glu Pro Asn Gly Cys
1               5                   10                  15
```

<210> SEQ ID NO 66
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

```
Ile Gly Leu His Asp Pro Thr Gln Gly Thr Glu Pro Asn Gly Cys
1               5                   10                  15
```

<210> SEQ ID NO 67
<211> LENGTH: 15
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 67

Ile Gly Leu His Asp Pro Thr Gln Gly Thr Glu Pro Asn Gly Cys
1               5                   10                  15

<210> SEQ ID NO 68
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Gly Leu His Asp Pro Thr Gln Gly Thr Glu Pro Ala Gly Glu
1               5                   10                  15

<210> SEQ ID NO 69
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ile Gly Leu His Asp Pro Thr Gln Gly Thr Glu Pro Ala Gly Cys
1               5                   10                  15

<210> SEQ ID NO 70
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ile Gly Leu His Asp Pro Thr Gln Gly Thr Glu Pro Ala Gly Cys
1               5                   10                  15

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ile Gly Leu His Asp Pro Thr Gln Gly Thr Glu Pro Ala Gly Cys
1               5                   10                  15

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ile Gly Leu His Asp Pro Thr Gln Gly Thr Glu Pro Ala Gly Cys
1               5                   10                  15

<210> SEQ ID NO 73

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ile Gly Leu His Asp Pro Ser His Gly Thr Leu Pro Ala Gly
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ile Gly Leu His Asp Pro Ser His Gly Thr Leu Pro Asn Gly
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ile Gly Leu His Asp Pro Ser His Gly Thr Leu Pro Asn Gly
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ile Gly Leu His Asp Pro Ser His Gly Thr Leu Pro Asn Gly
1               5                   10

<210> SEQ ID NO 77
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ile Gly Leu His Asp Pro Ser His Gly Thr Leu Pro Asn Gly
1               5                   10

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78
```

Ile Gly Leu His Asp Pro Ser His Gly Thr Leu Pro Gln Gly Ser
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Ile Gly Leu His Asp Pro Ser His Gly Thr Leu Pro Asp Gly Ser
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ile Gly Leu His Asp Pro Ser His Gly Thr Leu Pro Glu Gly Ser
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ile Gly Leu His Glu Pro Ser His Gly Thr Leu Pro Asn Gly Ser
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ile Gly Leu His Gln Pro Ser His Gly Thr Leu Pro Asn Gly Ser
1               5                   10                  15

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ile Gly Leu His Asn Pro Ser His Gly Thr Leu Pro Asn Gly Ser
1               5                   10                  15

<210> SEQ ID NO 84
<211> LENGTH: 15
<212> TYPE: PRT
<213> ORGANISM: Artificial Sequence
<220> FEATURE:

<223> OTHER INFORMATION: Description of Artificial Sequence: Synthetic
        peptide

<400> SEQUENCE: 84

Ile Gly Leu His Glu Pro Ser His Gly Thr Leu Pro Ala Gly Ser
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 85

Ile Gly Leu His Gln Pro Ser His Gly Thr Leu Pro Ala Gly Ser
1               5                   10                  15

<210> SEQ ID NO 86
<211> LENGTH: 15
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 86

Ile Gly Leu His Asn Pro Ser His Gly Thr Leu Pro Ala Gly Ser
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 87

Ile Gly Leu His Asp Pro Ser His Gly Thr Leu Pro Gln Gly Ser Cys
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 88

Ile Gly Leu His Asp Pro Ser His Gly Thr Leu Pro Asp Gly Ser Cys
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 89

Ile Gly Leu His Asp Pro Ser His Gly Thr Leu Pro Glu Gly Ser Cys
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ile Gly Leu His Glu Pro Ser His Gly Thr Leu Pro Asn Gly Ser Cys
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ile Gly Leu His Gln Pro Ser His Gly Thr Leu Pro Asn Gly Ser Cys
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ile Gly Leu His Asn Pro Ser His Gly Thr Leu Pro Asn Gly Ser Cys
1               5                   10                  15

<210> SEQ ID NO 93
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ile Gly Leu His Asp Pro Ser His Gly Thr Leu Pro Gln Gly
1               5                   10

<210> SEQ ID NO 94
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ile Gly Leu His Asp Pro Ser His Gly Thr Leu Pro Asp Gly
1               5                   10

<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

```
Ile Gly Leu His Asp Pro Ser His Gly Thr Leu Pro Glu Gly
1               5                   10

<210> SEQ ID NO 96
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Ile Gly Leu His Glu Pro Ser His Gly Thr Leu Pro Asn Gly
1               5                   10

<210> SEQ ID NO 97
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ile Gly Leu His Gln Pro Ser His Gly Thr Leu Pro Asn Gly
1               5                   10

<210> SEQ ID NO 98
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Ile Gly Leu His Asn Pro Ser His Gly Thr Leu Pro Asn Gly
1               5                   10

<210> SEQ ID NO 99
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Ile Gly Leu His Glu Pro Ser His Gly Thr Leu Pro Ala Gly
1               5                   10

<210> SEQ ID NO 100
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ile Gly Leu His Gln Pro Ser His Gly Thr Leu Pro Ala Gly
1               5                   10

<210> SEQ ID NO 101
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 101

Ile Gly Leu His Asn Pro Ser His Gly Thr Leu Pro Ala Gly
1               5                   10

<210> SEQ ID NO 102
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ile Gly Leu His Asp Pro Ser His Gly Thr Leu Pro Gln Gly Glu
1               5                   10                  15

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ile Gly Leu His Asp Pro Ser His Gly Thr Leu Pro Asp Gly Glu
1               5                   10                  15

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ile Gly Leu His Asp Pro Ser His Gly Thr Leu Pro Glu Gly Glu
1               5                   10                  15

<210> SEQ ID NO 105
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Ile Gly Leu His Glu Pro Ser His Gly Thr Leu Pro Asn Gly Glu
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ile Gly Leu His Gln Pro Ser His Gly Thr Leu Pro Asn Gly Glu
1               5                   10                  15
```

<210> SEQ ID NO 107
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ile Gly Leu His Asn Pro Ser His Gly Thr Leu Pro Asn Gly Glu
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ile Gly Leu His Glu Pro Ser His Gly Thr Leu Pro Ala Gly Glu
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ile Gly Leu His Gln Pro Ser His Gly Thr Leu Pro Ala Gly Glu
1               5                   10                  15

<210> SEQ ID NO 110
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Ile Gly Leu His Asn Pro Ser His Gly Thr Leu Pro Ala Gly Glu
1               5                   10                  15

<210> SEQ ID NO 111
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
                20                  25                  30

Ser Ile Gly Leu His Asp Pro Ser His Gly Thr Leu Pro Asn Gly Ser
            35                  40                  45

<210> SEQ ID NO 112
<211> LENGTH: 49

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Ala Glu Ala Ala
            20                  25                  30

Ala Lys Ile Gly Leu His Asp Pro Ser His Gly Thr Leu Pro Asn Gly
        35                  40                  45

Ser

<210> SEQ ID NO 113
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Gly Gly
            20                  25                  30

Ser Ile Trp Ile Gly Leu His Asp Pro Ser His Gly Thr Leu Pro Asn
        35                  40                  45

Gly Ser
    50

<210> SEQ ID NO 114
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Ile Gly Leu His Asp Pro Ser His Gly Thr Leu Pro Ala Gly Ser Gly
1               5                   10                  15

Gly Gly Gly Ser His Gly Glu Gly Thr Phe Thr Ser Asp Leu Ser Lys
            20                  25                  30

Gln Met Glu Glu Glu Ala Val Arg Leu Phe Ile Glu Trp Leu Lys Asn
        35                  40                  45

<210> SEQ ID NO 115
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Ile Gly Leu His Asp Pro Ser His Gly Thr Leu Pro Ala Gly Ser Gly
1               5                   10                  15

Gly Gly Gly Gly Gly His Gly Glu Gly Thr Phe Thr Ser Asp Leu Ser
            20                  25                  30

Lys Gln Met Glu Glu Glu Ala Val Arg Leu Phe Ile Glu Trp Leu Lys
        35                  40                  45

Asn

<210> SEQ ID NO 116
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Ile Gly Leu His Asp Pro Ser His Gly Thr Leu Pro Ala Gly Ser Ala
1               5                   10                  15

Glu Ala Ala Lys His Gly Glu Gly Thr Phe Thr Ser Asp Leu Ser
            20                  25                  30

Lys Gln Met Glu Glu Glu Ala Val Arg Leu Phe Ile Glu Trp Leu Lys
        35                  40                  45

Asn

<210> SEQ ID NO 117
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser Gly Gly Gly Gly Ser Ile Gly Leu His Asp Pro
        35                  40                  45

Ser His Gly Thr Leu Pro Asn Gly Ser
    50                  55

<210> SEQ ID NO 118
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser Ala Glu Ala Ala Ala Lys Ile Gly Leu His Asp
        35                  40                  45

Pro Ser His Gly Thr Leu Pro Asn Gly Ser
    50                  55

<210> SEQ ID NO 119
<211> LENGTH: 57
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 119

Ile Gly Leu His Asp Pro Ser His Gly Thr Leu Pro Ala Gly Ser Gly
1               5                   10                  15

Gly Gly Gly Ser Leu Leu Gly Asp Phe Phe Arg Lys Ser Lys Glu Lys
            20                  25                  30

Ile Gly Lys Glu Phe Lys Arg Ile Val Gln Arg Ile Lys Asp Phe Leu
        35                  40                  45

Arg Asn Leu Val Pro Arg Thr Glu Ser
    50                  55

<210> SEQ ID NO 120
<211> LENGTH: 58
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Ile Gly Leu His Asp Pro Ser His Gly Thr Leu Pro Ala Gly Ser Ala
1               5                   10                  15

Glu Ala Ala Lys Leu Leu Gly Asp Phe Phe Arg Lys Ser Lys Glu
            20                  25                  30

Lys Ile Gly Lys Glu Phe Lys Arg Ile Val Gln Arg Ile Lys Asp Phe
        35                  40                  45

Leu Arg Asn Leu Val Pro Arg Thr Glu Ser
    50                  55

<210> SEQ ID NO 121
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This sequence may encompass 1-4 "Gly Gly Gly
      Gly Ser" repeating units

<400> SEQUENCE: 121

Gly Gly Gly Gly Ser Gly Gly Gly Ser Gly Gly Gly Gly Ser Gly
1               5                   10                  15

Gly Gly Gly Ser
            20

<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: This sequence may encompass 1-3 "Glu Ala Ala
      Ala Lys" repeating units

<400> SEQUENCE: 122

Glu Ala Ala Ala Lys Glu Ala Ala Ala Lys Glu Ala Ala Ala Lys

-continued

```
1               5                   10                  15
```

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(8)
<223> OTHER INFORMATION: This sequence may encompass 6-8 residues

<400> SEQUENCE: 123

```
Gly Gly Gly Gly Gly Gly Gly Gly
1               5
```

<210> SEQ ID NO 124
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

```
Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Ala Lys Glu Ala
            20                  25                  30

Ala Ala Lys Glu Ala Ala Ala Lys Glu Ala Ala Ala Lys Ala
            35                  40                  45
```

<210> SEQ ID NO 125
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

```
Gly Gly Gly Gly Gly Gly Gly Gly
1               5
```

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

```
Gly Gly Gly Gly Gly Gly
1               5
```

<210> SEQ ID NO 127
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

```
Ala Glu Ala Ala Ala Lys Glu Ala Ala Lys Ala
1               5                  10
```

<210> SEQ ID NO 128
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

```
Pro Ala Pro Ala Pro
1               5
```

<210> SEQ ID NO 129
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(34)
<223> OTHER INFORMATION: This sequence may encompass 5-17 "Ala Pro"
      repeating units

<400> SEQUENCE: 129

```
Ala Pro Ala Pro Ala Pro Ala Pro Ala Pro Ala Pro Ala Pro Ala Pro
1               5                  10                  15
Ala Pro Ala Pro Ala Pro Ala Pro Ala Pro Ala Pro Ala Pro Ala Pro
            20                  25                  30
Ala Pro
```

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

```
Val Ser Gln Thr Ser Lys Leu Thr Arg Ala Glu Thr Val Phe Pro Asp
1               5                  10                  15
Val
```

<210> SEQ ID NO 131
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

```
Pro Leu Gly Leu Trp Ala
1               5
```

<210> SEQ ID NO 132
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 132

Thr Arg His Arg Gln Pro Arg Gly Trp Glu
1               5                   10

<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gly Gly Gly Gly Ser
1               5

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ala Glu Ala Ala Ala Lys
1               5
```